(12) United States Patent
Zielinski et al.

(10) Patent No.: US 10,859,558 B2
(45) Date of Patent: Dec. 8, 2020

(54) OILFIELD MONITORING OF SUBTERRANEAN POLYMER SOLUTION

(71) Applicant: SCHLUMBERGER TECHNOLOGY CORPORATION, Sugar Land, TX (US)

(72) Inventors: Lukasz Zielinski, Somerville, MA (US); Andrew Clarke, Cambridge (GB); Valerie Anderson, Cambridgeshire (GB); Gerald Henry Meeten, Cambridge (GB); Andrew William Meredith, Cambridge (GB)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 307 days.

(21) Appl. No.: 15/768,263

(22) PCT Filed: Oct. 12, 2016

(86) PCT No.: PCT/US2016/056485
§ 371 (c)(1),
(2) Date: Apr. 13, 2018

(65) Prior Publication Data
US 2018/0306765 A1    Oct. 25, 2018

Related U.S. Application Data

(60) Provisional application No. 62/240,949, filed on Oct. 13, 2015, provisional application No. 62/402,581, filed on Sep. 30, 2016.

(51) Int. Cl.
*E21B 49/08* (2006.01)
*E21B 47/10* (2012.01)
(Continued)

(52) U.S. Cl.
CPC ......... *G01N 33/2823* (2013.01); *E21B 49/08* (2013.01); *E21B 49/082* (2013.01);
(Continued)

(58) Field of Classification Search
CPC ...... C09K 8/588; C09K 8/68; C09K 2208/10; C09K 8/512; C09K 8/035; E21B 43/26; E21B 47/1015; E21B 49/00; E21B 43/16
See application file for complete search history.

(56) References Cited

U.S. PATENT DOCUMENTS

| | | |
|---|---|---|
| 2010/0126717 A1 | 5/2010 | Kuchuk et al. |
| 2013/0284894 A1 | 10/2013 | Freese et al. |
| 2014/0024073 A1 | 1/2014 | Zhdaneev et al. |

FOREIGN PATENT DOCUMENTS

| | | |
|---|---|---|
| WO | 01-31328 A1 | 5/2001 |
| WO | 2015094351 A1 | 6/2015 |

OTHER PUBLICATIONS

International Search Report and Written Opinion for corresponding PCT/US2016/056485, dated Jan. 24, 2017, 16 pages.

*Primary Examiner* — Zakiya W Bates

(57) ABSTRACT

Aqueous liquid which has been in contact with a subterranean geological formation, especially a hydrocarbon reservoir, is examined in order to detect or measure viscosifying polymer therein, by flowing a sample of the liquid through a constriction thereby causing extensional flow and alignment of any polymer molecules with the flow, and examining the solution for birefringence of aligned polymer molecules. The amount of birefringence is determined from intensity of light which has passed through the solution relative to intensity of the light source.

20 Claims, 10 Drawing Sheets

(51) Int. Cl.
*C09K 8/035* (2006.01)
*C09K 8/588* (2006.01)
*G01N 33/28* (2006.01)
*G01N 21/23* (2006.01)
*G01N 21/85* (2006.01)
G01N 21/05 (2006.01)
E21B 43/16 (2006.01)
E21B 43/26 (2006.01)

(52) U.S. Cl.
CPC ........... *E21B 49/086* (2013.01); *G01N 21/23* (2013.01); *G01N 21/85* (2013.01); *E21B 43/16* (2013.01); *E21B 43/26* (2013.01); *E21B 49/0875* (2020.05); *G01N 21/05* (2013.01)

OILFIELD MONITORING OF SUBTERRANEAN POLYMER SOLUTION

CROSS-REFERENCE TO RELATED APPLICATION

This application claims priority to and the benefit of a US Provisional applications having Ser. No. 62/240,949, filed 13 Oct. 2015 and on a US Provisional application having Ser. No. 62/402,581, filed 30 Sep. 2016 which are incorporated by reference herein.

FIELD AND BACKGROUND

Some aspects of the present disclosure relate to apparatus and methods for observing polymer in liquids which are or have been exposed to geological formations and associated formation liquids below ground.

In some procedures in connection with production of hydrocarbons from underground reservoirs, a viscosified aqueous liquid, which may be viscosified water or viscosified brine, is pumped down a borehole into contact with the subterranean formation and the fluid which is naturally present in the formation.

One procedure in which this occurs is enhanced oil recovery using a polymer flood. Enhanced oil recovery ("EOR") is an umbrella term covering a wide range of techniques used to improve the hydrocarbon recovery factor over and above the regular methods of providing for oil recovery from hydrocarbon reservoirs. A typical chemical EOR project begins with a period of screening, which may involve laboratory tests on both reservoir core samples and reservoir fluids as well as downhole tests known as micro-pilots, during which potential chemical formulations for performing the EOR are tested. This is followed by reservoir modeling of the projected effect of the EOR flood, the injection of the EOR liquids (the chemical formulation), on the ultimate recovery factor. The procedure which is eventually chosen may be a polymer flood, or may include a polymer flood, in which a viscosified water or brine is pumped into the reservoir through an injection well and drives oil through the reservoir to one or more receiving wells where the oil, accompanied by an aqueous phase, is produced to the surface.

Viscosification of water or brine may be brought about with a long chain linear polymer, typically with molecular mass in the range $10^5$ to $2\times10^7$ Dalton (Da). The viscosification efficiency of such polymer is linked to the large molecular mass. Typically a few percent (%) of polymer, possibly less than 1%, can increase the solvent viscosity by factors of $10^2$ to $10^4$. One example of polymer is water-soluble partially hydrolysed polyacrylamide. Others include guar, chemically modified guar and xanthan.

Propagation of the polymer flood may be monitored. The monitoring techniques used today include cross-well seismic tomography—which is sensitive to the changes in the acoustic response of the formation following the invasion of the flood liquids—and deep reading cross-well electromagnetic (EM) tomography, which detects the changes in the formation conductivity.

However, both techniques are limited in resolution and sensitivity. The EM method requires dense spacing of pilot wells to provide the required sensitivity, and the interpretation of seismic tomography is challenging depending on many unknown parameters. While both techniques respond to large scale changes in formation response that can be linked to formation fluid (oil) displacements, the techniques do not directly sense the fluids or the changes in the microscopic saturations or fluid configuration inside pore space in the reservoir rock. Consequently, pilot surveillance wells are typically drilled with the aim of directly intercepting and observing the flood as it passes the well.

In the surveillance wells, a range of standard downhole sensor tools may be used. Thus, depending on the type of flood, formation resistivity may be measured or formation density and porosity, or the ratio of carbon to oxygen may be measured for saturation estimation. If specialty non-conductive casing has been installed, nuclear magnetic resonance and dielectric measurements of the formation can give more insight into the fluid properties and fluid configuration inside the pore space. Eventually, the flood front and the displaced fluids reach the receiving wells where fluid is produced to the surface and the production rates can be monitored directly. However, these current techniques serve only to monitor the effects of the EOR flood and none of them directly observe the presence of the viscosified liquid pumped into the formation.

Another example of a procedure which uses viscosified water or brine is hydraulic fracturing. In this procedure, this viscosified liquid is pumped down a borehole and out into the surrounding formation at sufficient pressure to create and/or enlarge fractures in the formation. At least some of the aqueous liquid may enter the pores of a porous formation. When pressure from pumping is reduced, at least some fracturing fluid returns to the surface.

SUMMARY

This summary is provided to introduce a selection of concepts that are further described below in the detailed description. This summary is not intended to be used as an aid in limiting the scope of the claimed subject matter.

One aspect of the present disclosure provides a method of observing polymer in aqueous liquid which is or has been in contact with a subterranean geological formation. The method can be applied as a method of examining aqueous liquid to detect or measure polymer therein. The method comprises flowing some of the aqueous liquid, or possibly a solution into which polymer from the aqueous liquid has been extracted, through a constriction thereby causing extensional flow and alignment of polymer molecules (if present) in the flow, and observing at least one anisotropic physical property, which may be an optical or dielectric property, of aligned polymer molecules in the solution.

The subterranean geological formation may be a hydrocarbon reservoir. Observation of polymer may be qualitative detection of the presence of polymer or may be quantitative estimation of polymer concentration and/or molecular weight.

The method may be applied as a method of observing polymer used in an EOR polymer flood and this may be done in order to monitor progress of the flood through the reservoir.

Whether or not the method is being used to observe a polymer flood, some forms of the method disclosed herein may be carried out with liquid which is still underground. This may be done in a surveillance well to monitor the polymer flood passing that well. Alternatively the method may be carried out at the surface, examining liquid produced from below ground or collected as a sample below ground and brought to the surface.

Observation of an anisotropic optical property may be observation of birefringence. Birefringence is an optical property arising from anisotropy of refractive indices in different directions and is observed as a change in the polarization of light passing through the solution in which polymer molecules have been aligned by extensional flow.

Birefringence is a known phenomenon. It has been used as a qualitative observational technique in microscopy and it has also been used in the study of polymers and other materials. However, in the present disclosure it is used in a new and different way, namely for the detection or measurement of polymers in dilute solution. The present inventors have discovered that birefringence of polymer molecules in solution can be sufficiently sensitive to be used for measuring small concentrations of polymer and have recognised that it can differentiate from other materials present. Birefringence will only be observed from molecules which (i) have the property of birefringence and (ii) are large enough to align in the extensional flow. Some molecules which may be present in addition to the polymer of interest may not have any birefringence property at all. Small molecules which do have the property of birefringence will not be observed because they will not become aligned with the flow and so remain isotropic. The practical consequence is that the polymer used to enhance viscosity can be detected in the presence of other materials which have mixed with, or dissolved in, the aqueous liquid whilst that liquid was in contact with the geological formation and was able to mix with liquids naturally present in the formation.

In some forms of the method, the aqueous liquid may be purified to some extent so as to allow light to pass through it, for example by removing suspended solids and water-immiscible droplets, but a state of chemical purity is not needed and dissolved substances which do not prevent transmission of light may be left in solution. Thus when the solution flows through the constriction it may still contain salts from the geological formation to which the aqueous liquid was exposed.

If examination for birefringence is carried out below ground, such as in a surveillance well, the aqueous solution which flows through a constriction to align polymer molecules may be aqueous liquid drawn from the formation. If examination for birefringence is carried out at the surface, to observe polymer in aqueous liquid brought to the surface from below ground, some of this liquid may be the aqueous solution which is made to flow through a constriction to align polymer molecules.

However, it is also possible that the method includes a step in which any polymer dissolved in aqueous liquid brought to the surface is are extracted into another solvent and then it is the solution in this other solvent which is made to flow through the constriction and is examined for birefringence.

Observation of an anisotropic dielectric property may be measurements of permittivity or conductivity in two directions which may be orthogonal to each other and to the direction of flow. Measurements may be made by applying high-frequency signals to electrodes so as to create alternating electric fields between the electrodes.

Another aspect of the present disclosure is specifically concerned with EOR processes. This aspect of the disclosure provides a method of hydrocarbon recovery from a reservoir comprising pumping a liquid down an injection wellbore into the reservoir so that the liquid moves through the reservoir, driving oil to receiving wells where the oil is produced to the surface, in which method sensors able to observe the liquid or a constituent of that liquid are provided at downhole locations spaced from the injection well so as to be able to observe the liquid or a constituent of the liquid when the liquid arrives from the injection wellbore.

The sensors may be located downhole in surveillance wells and in this aspect of the disclosure the injected liquid may be other than a polymer solution. Possibilities for the liquid which is pumped down the injection borehole include $CO_2$, natural gas, methane, low-salinity water, alkaline and surfactant solutions.

In embodiments of the present disclosure, an EOR tool can be modular and configurable in the sense that it can consist of one or more sensors sensitive to one or more specific EOR chemicals or some aspects or a particular property of that chemical. The EOR tool or any of its modules may be deployed at any stage in the EOR project cycle, including both surface and downhole measurements, both at the injector well and any pilot or surveillance wells, as well as any development and production wells, both in the drilling stage and production stage, both in open and cased holes. It can be deployed on any platform available for making oilfield measurements. This includes, but is not limited to, the conveyance by wireline, slickline, coiled tubing, while-drilling conveyance, any distributed sensing scheme, both on fiber optic and electrical cable, where the whole string of sensors could be lowered into the well and remain there for an arbitrary period of time; any sensors embedded in the completion itself, both permanently or exchangeably, or in cement, or in other downhole hardware such as pumps, valves, flowmeters; or at any stage in the flow line or liquid handling system at surface or subsea, including any pipes, pumps, blowout preventers, separators, pipelines, flowmeters etc; or at the mixing pools where the chemicals are prepared at the injector.

In some forms of the present disclosure an EOR sensor or tool may be used to monitor the EOR liquid supplied in what is called a Micropilot process, where a well is logged—using for example nuclear magnetic resonance tools, dielectric tools and/or the like—a test volume of the EOR liquid is injected into the reservoir, and the well is logged again to assess the sweep efficiency of the EOR liquid. This process is used to calculate the efficiency of the selected EOR liquid prior to using the EOR liquid in a full scale flood process.

DETAILED DESCRIPTION

Figure 1:
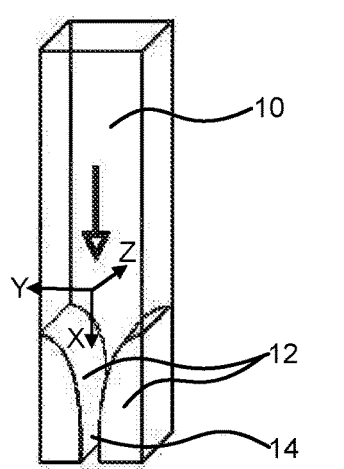
FIG. 1 schematically illustrates a duct shaped to give extensional flow.

Viscosified liquids used in oilfield processes in which the liquid is pumped down a well bore and out into contact with underground geological formation and formation liquids may be an aqueous solution of a polymer of large molecular mass M which has a substantially linear polymer chain formed of repeat units of relatively small molecular mass m which are connected one to the next by single covalent bonds which allow rotation of the repeat units relative to one another.

The repeat unit may be essentially rigid while the large flexibility of the polymer chain results from intra-molecular rotation of the chemical bonds that connect the repeat units. The degree of polymerization $N=M/m$ is the number of repeat units per chain. Ignoring any effects of chain stiffness for the purpose of explanation, for a repeat unit of length $l_0$ the maximum or fully-extended end-end distance of a chain is:

$$l_{FE}=N\times l_0 \qquad (1)$$

An isolated chain is not fully extended, but owing to the randomizing effect of entropy adopts a randomly coiled configuration such that in a quiescent solution the randomly-coiled end-to-end distance is $$l_{RC}=N^{1/2}\times l_0 \qquad (2)$$

While the present disclosure is not limited to specific polymer make up, a linear polymer may possibly have a mean molecular mass M of at least $10^5$ Da, possibly at least $10^6$ Da or even more such as at least $3.5\times10^6$ Da. A repeat unit may have a molecular mass m of not more than 300 Da, possibly not more than 100 Da.

For a polymer chain of molecular mass $M=2\times10^7$ Dalton (Da) formed of repeat units of mass $m=100$ Da (such that $N=2\times10^5$) the randomly coiled end-to-end distance is $$l_{RC}=(2\times10^5)^{1/2}\times l_0=447 l_0 \qquad (3)$$

This contrasts strongly with $l_{FE}=2\times10^5\times l_0$ for the fully-extended polymer, i.e. the ratio $l_{FE}/l_{RC}=N^{1/2}=447$. Polymer chains diluted in a solvent can be partially uncoiled during flow to obtain an end-to-end distance (l) such that $l_{RC}<l<l_{FE}$.

The present disclosure detects or measures polymers in aqueous solution by characteristics of the polymer chains which lead to anisotropic physical, notably optical or dielectric, properties when the polymer molecules are no longer positioned randomly but are brought into alignment or partial alignment.

The ability of a long chain polymer to give rise to anisotropic properties is illustrated by polyacrylamide which has a structure represented by the formula

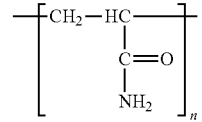

where the portion in square brackets is one repeat unit.

Each repeat unit is taken to possess a permanent electric dipole vector on account of the charge asymmetry associated with its intramolecular chemical bonds. A component $\mu_0$ of the permanent electric dipole vector per repeat unit will be parallel to the length 10 of the repeat unit. The components $\mu_0$ cumulate along the polymer chain and the fully-extended chain dipole moment is given by a formula analogous to equation (1) above, namely:

$$\mu_{FE}=N\times\mu_0. \qquad (4)$$

The randomly-coiled dipole moment is given by the formula:

$$\mu_{RC}=N^{1/2}\times\mu_0 \qquad (5)$$

Polarizability is observable when the polymer solution is subjected to an electric field. In a static field, or alternating field created by low-frequency alternating current, polarizability comes from alignment of permanent dipoles with the electric field and also from the ability of an electric field to displace charge within a molecule and induce a dipole moment. At high frequencies which alternate too fast for alignment of permanent dipoles with the electric field, polarizability is predominantly displacement of charge within a molecule, giving induced dipole moments. Polarization can be brought about by electromagnetic radiation, in other words by light, which of course includes a very high-frequency alternating electric field.

Polarization within a polymer repeat unit has a component parallel to the length of a repeat unit and these components cumulate along the length of a polymer chain in similar manner to the components of permanent dipole moment and polarization can be anisotropic with induced dipole moments cumulating along the polymer chain while induced dipole moments perpendicular to the chain length remain randomly oriented around the chain.

In order to observe anisotropic properties of polymer molecules, a solution containing the polymer is subjected to extensional flow. This may be done by directing a flow of liquid through a constriction so that the flow accelerates as it enters the constriction and the solution undergoes extension.

FIG. 1 shows a flow duct shaped to bring about extensional flow. The upper part 10 of the duct has a square cross section. In the lower part of the duct, two inserts 12 provide hyperbolic curved surfaces leading to a slot 14. Flow is downwards along the direction of the x axis. There is extension in the direction of the x axis as the flow enters the constriction and simultaneous contraction on the y axis. There is no change on the z axis. The effect of the extensional flow is to align polymer molecules towards an orientation in which they are parallel to the x axis, which is the flow direction.

Anisotropic polarizability of polymer molecules may be observed as the phenomenon of birefringence which is related to the polarizability of the polymer molecule. Because of the anisotropic polarizability, the polymer solution has different refractive indices in two orthogonal directions which in the present case are along the flow direction and perpendicular to it. When a beam of polarized light is directed through the solution at a position where the polymer molecules are aligned (or at least approximately aligned) with the direction of extensional flow, the velocities of light in two orthogonal directions are no longer the same and the angle of polarization is altered. The light with altered polarization can be observed and measured.

The theory of birefringence induced by extensional flow is known. Here it is summarized in the simplified case of a close refractive index match between the solvent and the polymer chain. The relevant property of the polymer chain is its anisotropy of optical polarizability, given by:

$$\gamma_1 - \gamma_2 = \frac{3}{5}(\alpha_1 - \alpha_2)\frac{l^2}{l_{RC}^2} \tag{6}$$

where: $\gamma_1$ and $\gamma_2$ are optical polarizabilities of a polymer chain in two orthogonal directions, i.e. along the polymer chain and a direction transverse to it, so that $\gamma_1$-$\gamma_2$ is the anisotropy of optical polarizability of a polymer molecule and $\alpha_1$ and $\alpha_2$ are optical polarizabilities of a repeat unit in the same two orthogonal directions, so that $\alpha_1$-$\alpha_2$ is the anisotropy of optical polarizability of a repeat unit, this being a property intrinsic to the chemical structure of the repeat unit and dependent on the orientation and conformation of the chemical bonds that comprise the repeat unit.

Polarizability $\gamma$ of a molecule is related to refractive index n by the well-known Lorentz-Lorenz relation:

$$\frac{n^2 - 1}{n^2 + 2} = \frac{4\pi v}{3M}\gamma = \frac{4\pi c N_A}{3M}\gamma \tag{7}$$

where v is the number density of polymer molecules, c is the polymer concentration (in g cm$^{-3}$) $N_A$ is Avogadro's number and M is molecular mass. Using this formula for the polarizabilities $\gamma_1$ and $\gamma_2$ gives:

$$\frac{n_1^2 - 1}{n_1^2 + 2} - \frac{n_2^2 - 1}{n_2^2 + 2} = \frac{4\pi c N_A}{3M}(\gamma_1 - \gamma_2) \tag{8}$$

where $n_1$ and $n_2$ are the principal refractive indices and where for dilute polymer solutions the difference between $n_1$ and $n_2$ is small. From equations above, the birefringence which is difference in refractive indices in orthogonal directions is given by $\Delta n = n_1 - n_2$ and:

$$\Delta n = \frac{2\pi c N_A}{15Mn}(n_I^2 + 2)^2(\alpha_1 - \alpha_2)\frac{l^2}{l_{RC}^2} \tag{9}$$

where $n_I$ is the isotropic refractive index of the solution.

Thus the birefringence of the light signal is a difference in refractive indices which is proportional to both the polarizability anisotropy of the polymer and the concentration of polymer molecules and inversely proportional to molecular mass of the polymer.

It is possible to measure the difference in refractive indices directly, by measuring the retardation of light in one direction relative to light in the orthogonal direction. Measuring equipment with this capability is available from Hinds Instruments, USA and such equipment may be used for measurements in accordance with the present disclosure.

However, in the present context of dilute polymer solutions, the rotation of the plane of polarization of light by the polymer solution is small and the magnitude of the birefringence can be determined from the ratio of the intensities of transmitted and received light when the liquid sample is between crossed polarizing filters. This is done in the apparatus described below with reference to FIGS. 2 to 10. When light from the light source is polarized at 45 degrees to the flow direction, which is convenient because it gives greatest sensitivity for crossed polarizing filters, the relationship between light intensity and birefringence is given by the equation $$J = \frac{J_0}{4}\left(1 - \cos\frac{2\pi dn}{\lambda}\right) \tag{10}$$

where $\lambda$, is the wavelength, d is the optical path length through the polymer solution, $J_0$ is the incident light intensity and J is intensity of light falling on the detector. For a small birefringence, as is the case here, the equation reduces to $$J = \frac{J_0}{8}\left(\frac{2\pi dn}{\lambda}\right)^2 \tag{11}$$

These equations allow birefringence $\Delta n$ to be calculated from measurements of light intensity. If the rate of flow through a constriction is kept to a constant value, the system can be calibrated using solutions of polymer of known concentration.

Figure 7:
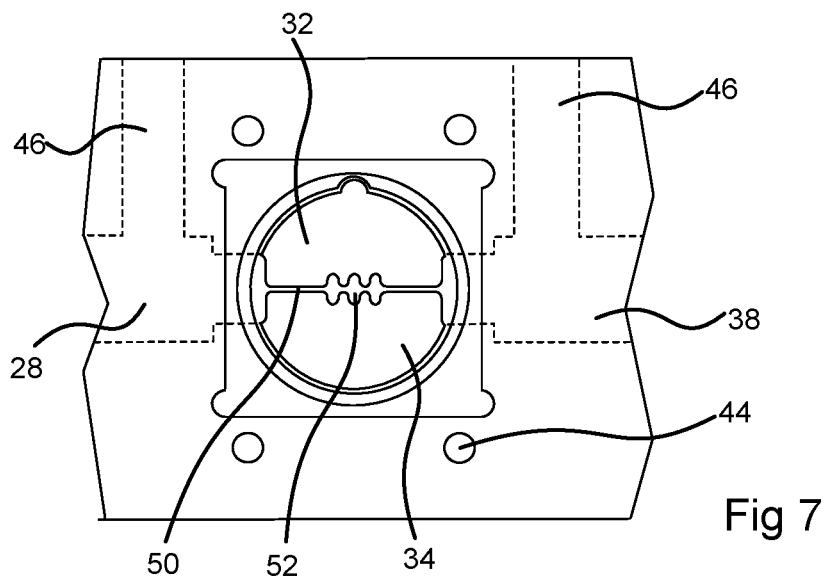
FIG. 7 is a similar view to FIG. 5, showing a modification.
Figure 8:
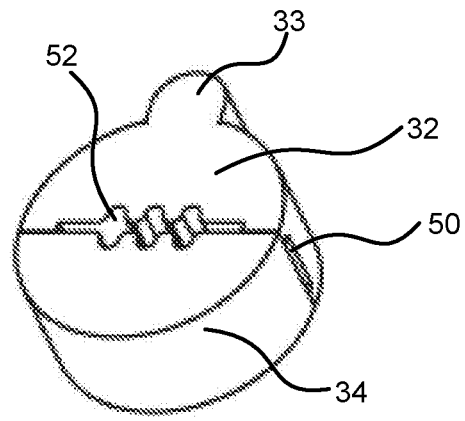
FIG. 8 is a perspective view of the additional parts which define the flow constriction within the central aperture in FIG. 7.
Figure 9:
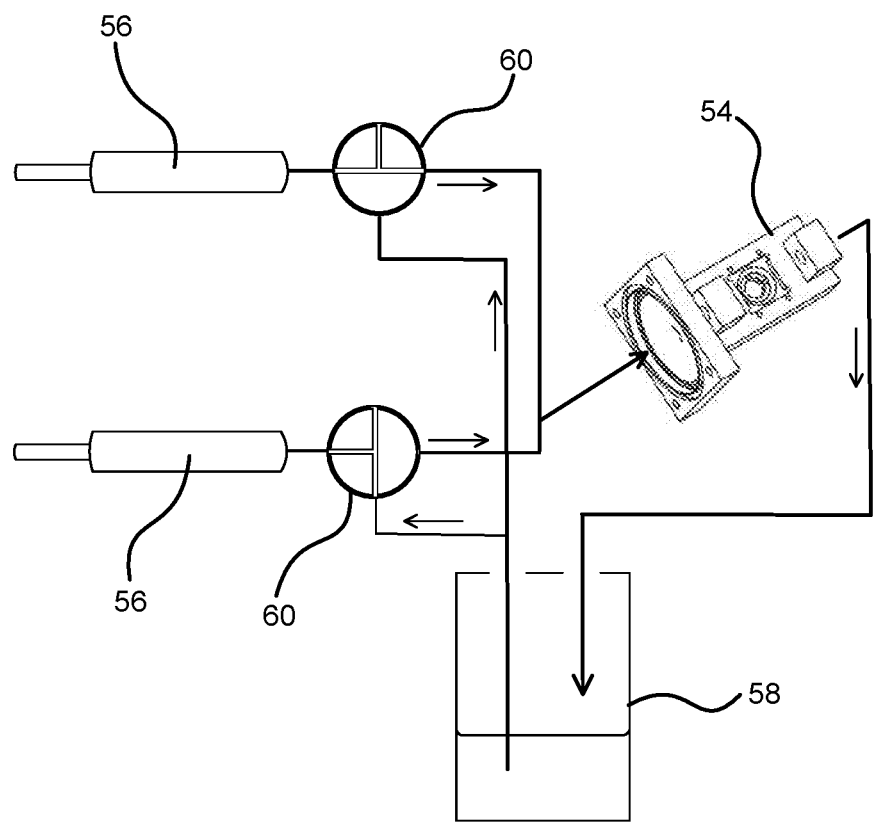
FIG. 9 diagrammatically shows pumps for supplying liquid to a flow cell.
Figure 10:
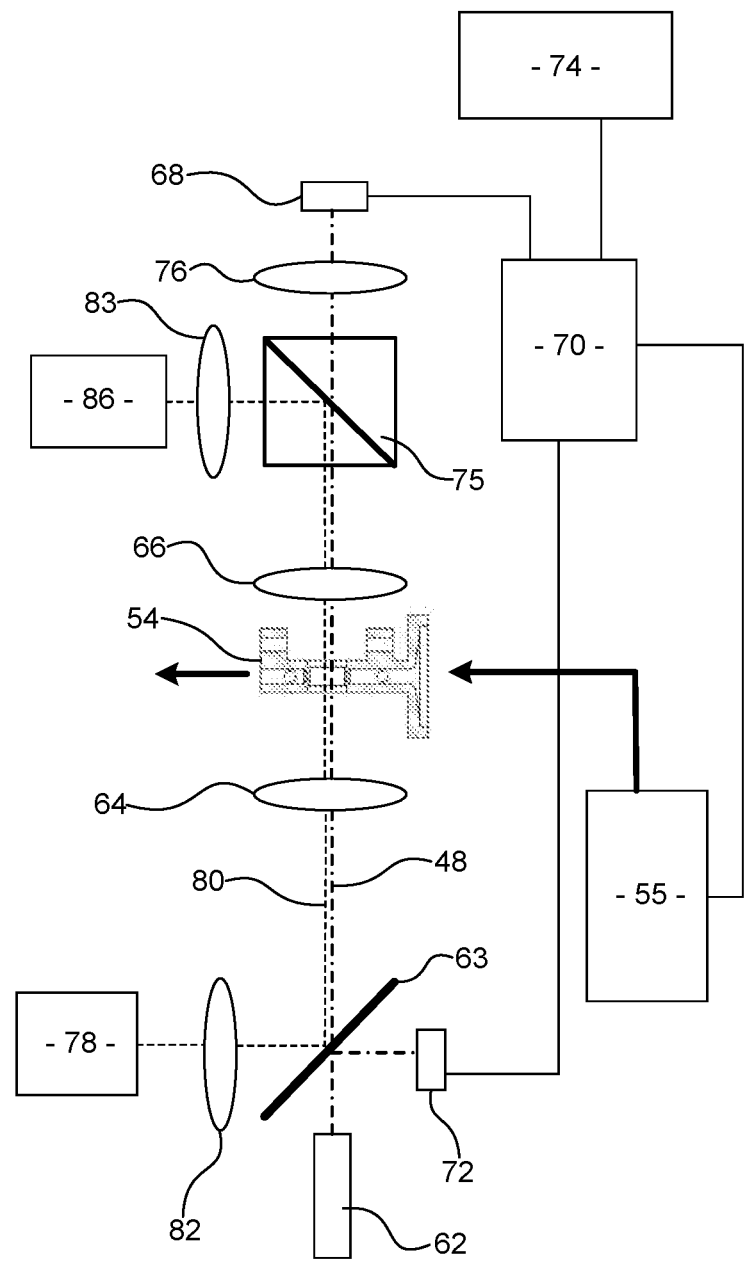
FIG. 10 is a diagrammatic view of apparatus for examining birefringence in flow through a cell.

Apparatus for carrying out the method will now be described with reference to the drawings in which FIGS. 2-6 show a cell for subjecting a liquid to extensional flow. FIGS. 7 and 8 show a similar cell with a different flow constriction. FIGS. 9 and 10 show an arrangement for examining the flow through either of those cells using polarized light so as to observe birefringence.

Figure 2:
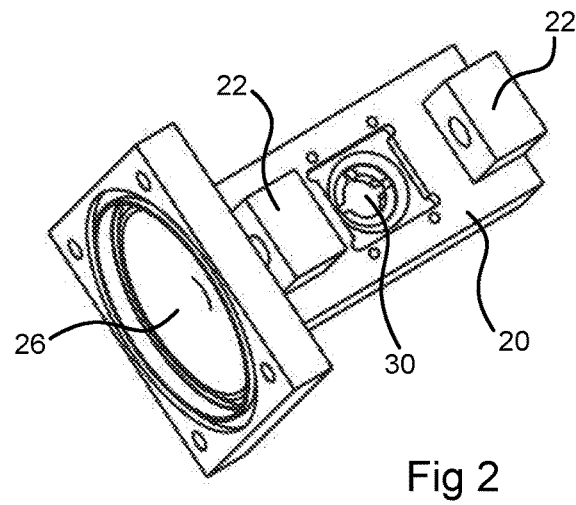
FIG. 2 is a perspective view of the main body of a flow cell for extensional flow of a liquid.
Figure 3:
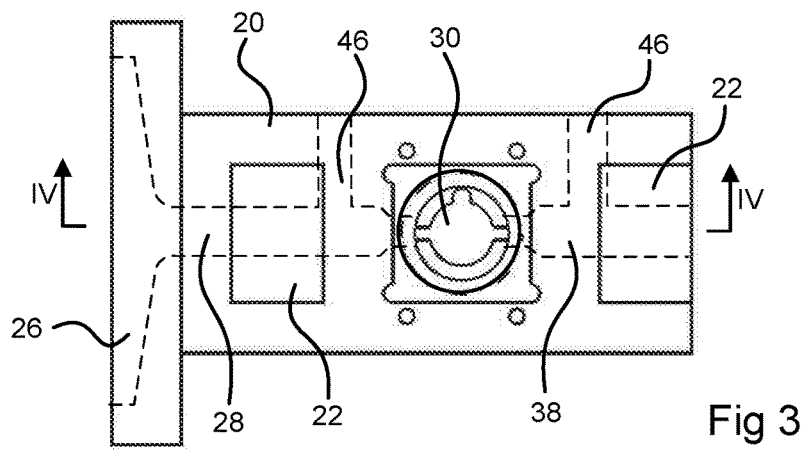
FIG. 3 is a side view of the main body shown in FIG. 2.
Figure 4:
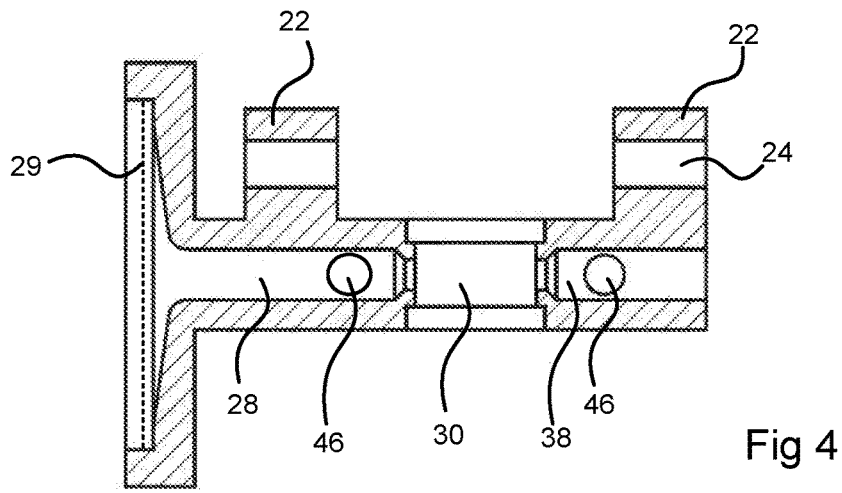
FIG. 4 is a section on line IV-IV of FIG. 3

The main body of a flow cell seen in FIGS. 2, 3 and 4 may be made by conventional machining or made in one piece by 3D printing. The main body comprises a cuboid 20 on which there are two smaller cubes 22 with through holes 24 used for attachment to other parts of the apparatus. The cell has a large mouth 26 connected to a through bore 28 leading to a central aperture 30. At the mouth 26, a filter 29 consisting of 35 micron nylon net filter cloth acts to disrupt any pattern of flow present in the incoming liquid.

Figure 5:
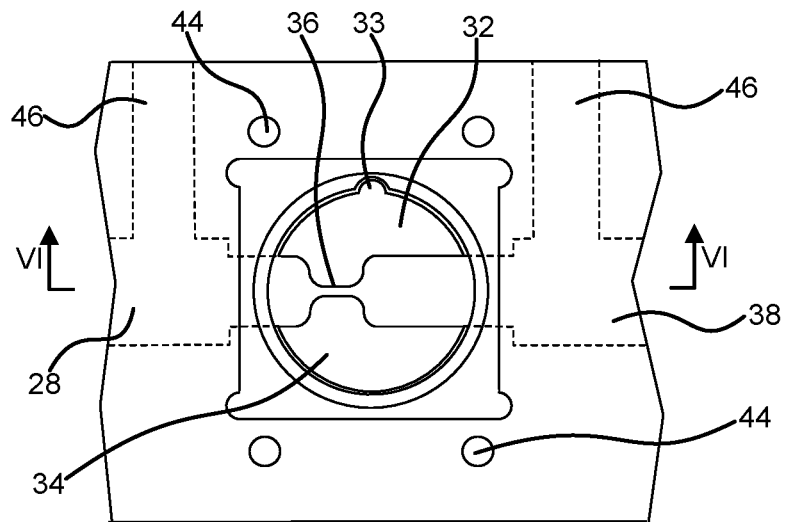
FIG. 5 is an enlarged view onto part of the main body of FIG. 2, showing the central aperture and inserted additional parts.

As shown by the enlarged view which is FIG. 5, two semi-cylindrical further parts 32, 34 are fitted into the central aperture 30. A lug 33 on part 32 engages a cut out in body 20. These additional parts 32, 34 define a narrow slot 36 through which flows liquid entering from the bore 28. Liquid which has passed through slot 36 flows into an exit bore 38. Flow into the slot 36 is extensional flow which brings polymer molecules in the liquid into alignment with the direction of flow.

Figure 6:
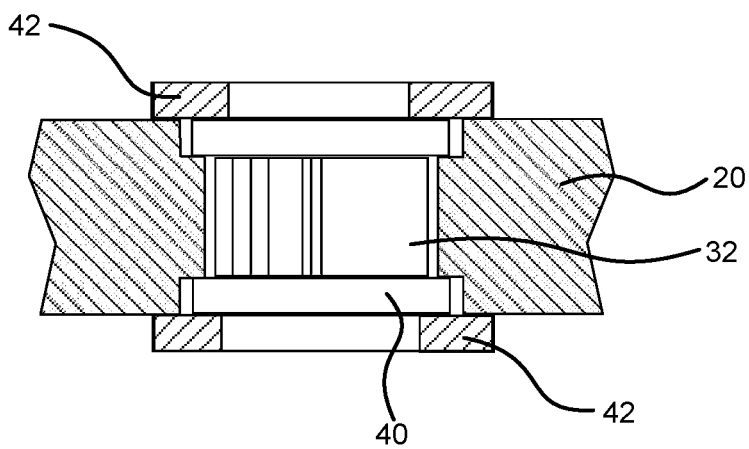
FIG. 6 is a section on line VI-VI of FIG. 5

FIG. 6 is a sectional view illustrating the assembly of additional parts at the central aperture 30 of body 20. The further part 32 which defines one side of the slot 36 is visible. Above and below the parts 32, 34 there are optically transparent windows 40 which abut the parts 32, 34 so as to close the upper and lower edges of the slot 36 defined between the parts 32, 34. Above and below the windows 40 there are two plates 42 each with a central aperture so that the windows are not obscured. These plates 42 are bolted to each other and to the main body 20 by bolts through the holes 44 so that the plates 42 hold the windows 40 and the parts 32, 34 in place. A thin gasket of soft material (not shown) with cut outs where required to allow passage of a light beam may be placed between the parts 32, 34 and each window 40 to provide a seal against liquid leakage and a further gasket of soft material may be provided between the windows 40 and the plates 42. This assembly is constructed to hold the windows 40 in place whilst minimizing stress on these windows so as to avoid stress induced birefringence of the windows 40.

The bores 28, 38 upstream and downstream of the slot 36 have side branches 46 connected to pressure sensors (not shown) so that the pressure drop across the slot 36 can be measured. The optically transparent windows 40 allow a light beam 48 to pass through the gap between the parts 32, 34 at a position which is sufficiently close to the slot 36 that the extensional flow into the slot has aligned polymer molecules with the direction of flow.

FIG. 7 shows a variation on the arrangement above. The parts 32, 34 fitted into the central aperture define between them a slot 50 which widens at three places 52. A light beam 48 is directed through the flow at one of these wider places. FIG. 8 shows the two parts 32, 34 from FIG. 7 fitted together. One end of the slot 50 is visible.

FIG. 10 diagrammatically illustrates apparatus for examining the flow through a slot 36 for birefringence. A flow cell as shown by FIGS. 2-6 or FIGS. 7 and 8 is indicated at 54. Liquid is pumped through the cell 54 by a pumping system 55 shown in more detail in FIG. 9. There are two syringe pumps 56 which operate alternately to draw liquid in from a supply 58 and pump it out through solenoid valves 60. The operation of the pumps and valves 56, 60 is controlled by the electronic package 70 shown diagrammatically in FIG. 10.

The apparatus shown in FIG. 10 allows birefringence to be seen visually and also allows it to be measured. In order to allow birefringence to be observed/measured, the apparatus directs a beam of light through one or more optical components that generate a defined polarization state then through the solution in the vicinity of the constriction such that any polymer molecules in the solution are aligned with the flow, then through one or more optical components that enable determination of the resultant polarization state. Then the solution birefringence is determined from the resultant polarization state. In this embodiment the component which generates a defined polarization state is a linear polarizing filter and so is the component which enables determination of the polarization state. But there are other possibilities, in particular circular polarizing filters could be used.

Referring to FIG. 10, a light source 62 which is a laser directs a beam 48 of monochromatic light of wavelength 655 nm through a dichroic mirror 63 to a linear polarizing filter 64 which plane polarizes the light. The light then passes through a flow cell 54 of the type shown in FIGS. 2 to 8. The light beam 48 is perpendicular to the direction of liquid flow. The plane of polarization of the light is arranged to be at 45° to the direction of liquid flow.

The light beam 48 next comes to a second polarizing filter 66 (which may be referred to as the analyser) oriented so that its plane of polarization is at 90° to that of the first polarizer. Consequently, if the cell is empty or contains a solution in which there is no polymer, no light passes through the second polarizing filter 66.

However, if there is birefringent polymer in the flow through the slot 36 of the cell 54, it rotates the plane of polarization of light in the beam, so that light does pass through the second polarizer 66 and then onwards through a beam splitter 75 and a 655 nm filter 76 to a photodiode 68. This photodiode 68 is connected to an electronics package 70 operating the photodiode 68 to measure the light intensity. A constant proportion of the light from the laser 62 is reflected from the back of the dichroic mirror 63 onto another photodiode 72 which is also connected to the electronics package 70 and measures the intensity of this light diverted by the dichroic mirror 63. The electronics package thus receives as inputs the intensity of light transmitted by the laser 62 and the intensity of light received by the photodiode 68, and a computer 74 connected to the electronics package 70 is able to calculate the ratio of these intensities and the birefringence.

In order to allow birefringence to be observed visually, a second light source 78 which is an LED transmits a beam 80 of green light through a 550 nm filter 82 to the dichroic mirror 63. From there it travels along the same path through the polarizing filters 64, 66 and the flow cell 54 between them before being directed by the beam splitter 75 through a second 550 nm filter 83 to a camera 86.

The visual system 78, 80, 86 allows birefringence of flowing polymer solutions to be seen as bright regions in a dark field. It is not necessarily operated at the same time as the laser system, 62, 48, 66, 72 but the 655 nm filter 76 prevents green light from reaching the photodiode 66 and the 550 nm filter 83 prevents laser light from reaching the camera 86.

It may be desired to have a system which is only used for visual examination of polymer solutions for birefringence, for instance to detect when a polymer flood breaks through into a production well. In such a circumstance, the laser system 62, 48, 66, 72 would be omitted. Conversely, if it was desired only to measure birefringence, the visual system 78, 80, 86 would be omitted.

In experimental work using apparatus as described above, a number of measurements were made using solutions of various polymers. Intensity of light received at the photodiode was measured as a proportion of the light transmitted from the laser and the birefringence was calculated as difference in refractive indices.

Figure 11:
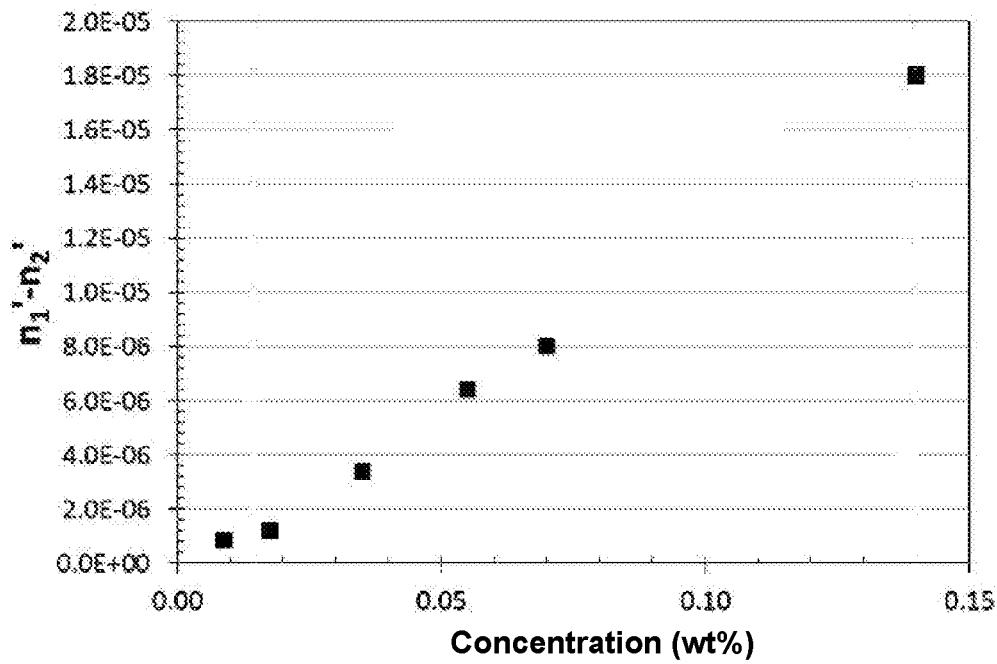
FIG. 11 is a graph of birefringence plotted against xanthan concentration.

Birefringence was measured for solutions of xanthan at a number of concentrations, using a flow rate through the cell of 100 ml/minute. Xanthan is a biopolymer with a double helix structure and is a relatively stiff molecule. It has no charge so is relatively insensitive to ionic strength. It has large polarizability of its repeat unit and hence a large birefringence when subjected to extensional flow. FIG. 11 shows birefringence plotted against concentration and this demonstrates that when measurements are made using the same polymer and with the same rate of flow through the cell for all measurements, the measured birefringence will be proportional to polymer concentration.

Birefringence was also measured for several solutions of partially hydrated polyacrylamide with various chain lengths. Values of birefringence measured using flow rates of 20 and 60 ml/minute are listed in the following table.

| Molecular mass | Concentration | Flow rate | Birefringence $n_1-n_2$ |
|---|---|---|---|
| 3.5 MDa | 0.6 wt % | 60 ml/min | 7.5E−07 |
| 12 MDa | 0.37 wt % | 60 ml/min | 1.7E−0.6 |
| 18 MDa | 0.13 wt % | 60 ml/min | 2.4E−0.6 |
| 18 MDa | 0.13 wt % | 20 ml/min | 4.0E−0.7 |
| 35 MDa | 0.064 wt % | 20 ml/Min | 9.0E−07 |

Figure 12:
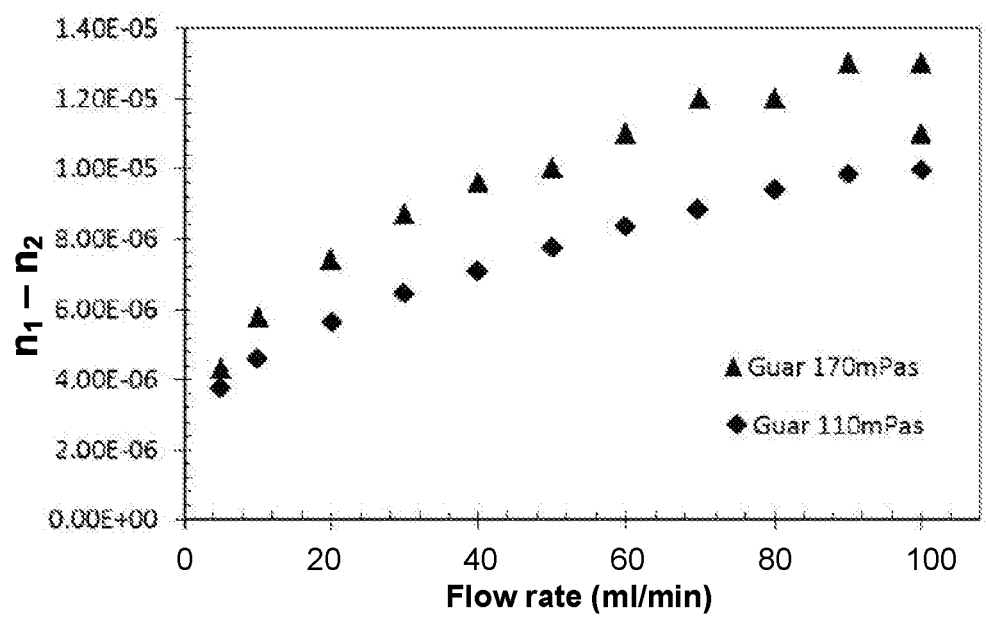
FIG. 12 is a graph of birefringence plotted against rate of flow through a flow cell, for two grades of guar.

It may also be useful to make measurements at more than one rate of flow. As flow rate through the constriction which is the slot 36 increases, the stress on the liquid will increase and uncoiling of the polymer chain will be greater, so that birefringence will increase even though the concentration remains constant. This is demonstrated by FIG. 12 which is a plot of birefringence calculated from measurements of light intensity for two grades of guar at a number of flow rates.

Birefringence which increases with flow rate through the cell will provide a qualitative indication or confirmation that the birefringence is attributable to the presence of polymer.

Figure 13:
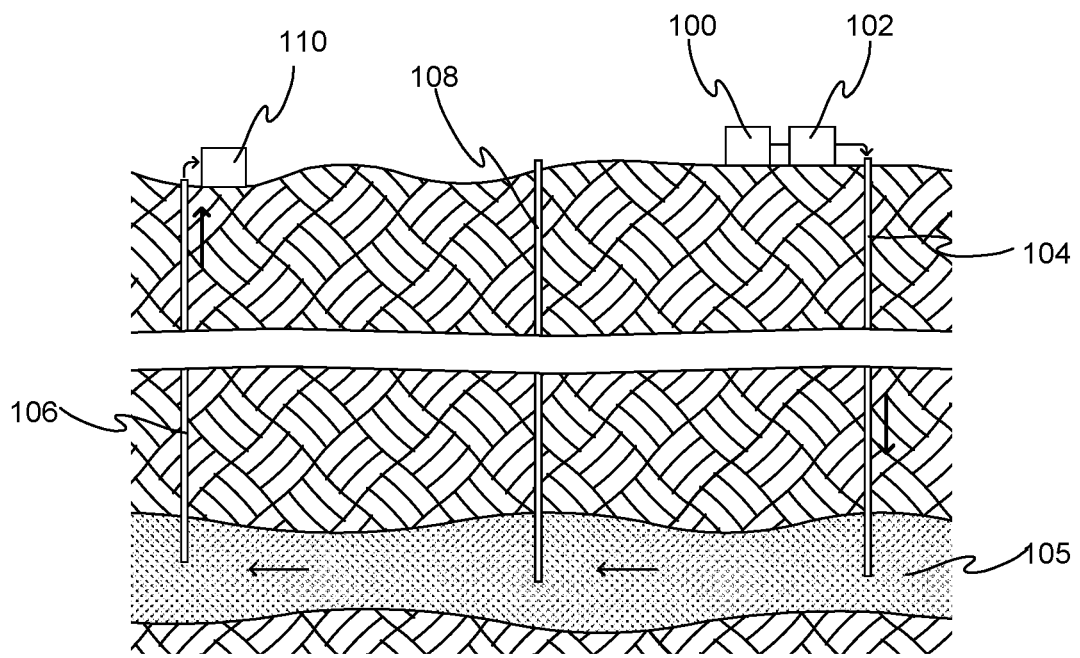
FIG. 13 is a section through the earth on line A-A of FIG. 14, schematically showing an EOR operation.
Figure 14:
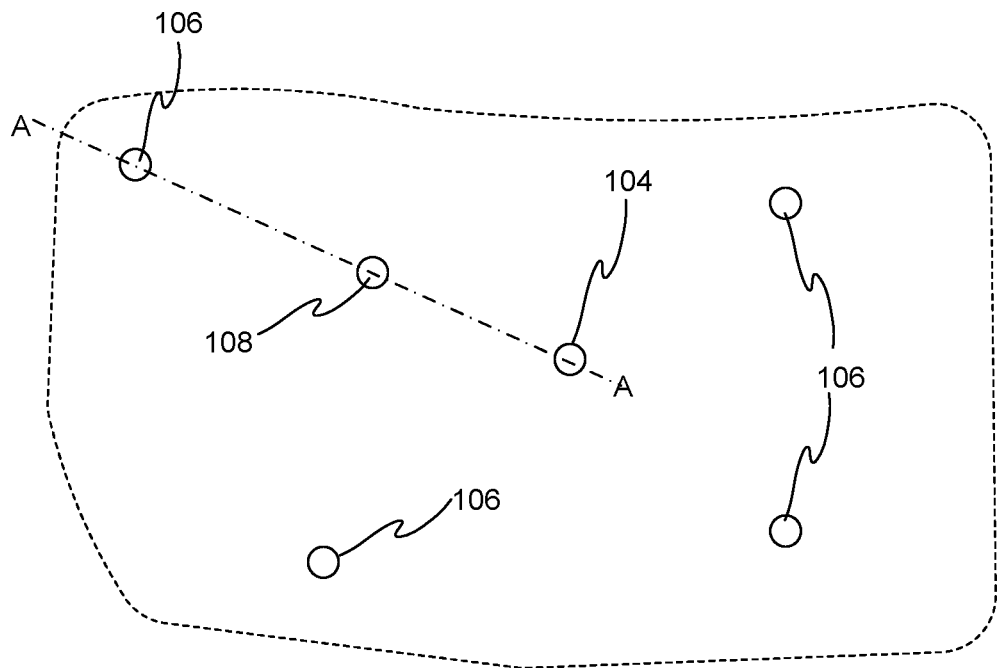
FIG. 14 is a plan view showing the positions of a number of wellbores.

FIGS. 13 and 14 show an illustrative arrangement of well for a polymer flood EOR operation where measurement of polymer by methods as above may be employed. An aqueous solution of a viscosifying polymer is mixed in plant 100 and pumped by means of pumps 102 down an injection well 104. This aqueous polymer solution, referred to as a polymer flood, flows outwardly from the injection well 104 into reservoir 105 pushing oil ahead of it so that oil mixed with an aqueous phase is produced at production wells 106 distributed around the injection well 104. A surveillance well 108 gives access to the reservoir at a location intermediate between the injection well 104 and one of the production wells 106.

The oil and aqueous phase produced at each of the wells 106 are separated by surface equipment 110 and a sample of flow from the aqueous phase is tested for birefringent polymer by means of the apparatus and method described with reference to FIGS. 2 to 10.

At the foot of the surveillance well 108 there may be equipment installed downhole which is able to take samples from the surrounding liquids and examine these for the presence of birefringent polymer by the method described above. Alternatively such equipment may take the form of a wireline tool which is lowered into the surveillance well from time to time. A further possibility is that a wireline is lowered into the surveillance well from time to time and used to collect a sample of downhole liquid which is brought to the surface by the wireline and examined for birefringence in the same manner as samples of the aqueous phase taken from the producer wells 106.

The arrangement of wells shown in FIGS. 13 and 14 is merely an illustration. A polymer flood could be carried out without any surveillance wells or alternatively carried out using more surveillance wells then the one well 108 shown.

Figure 15:
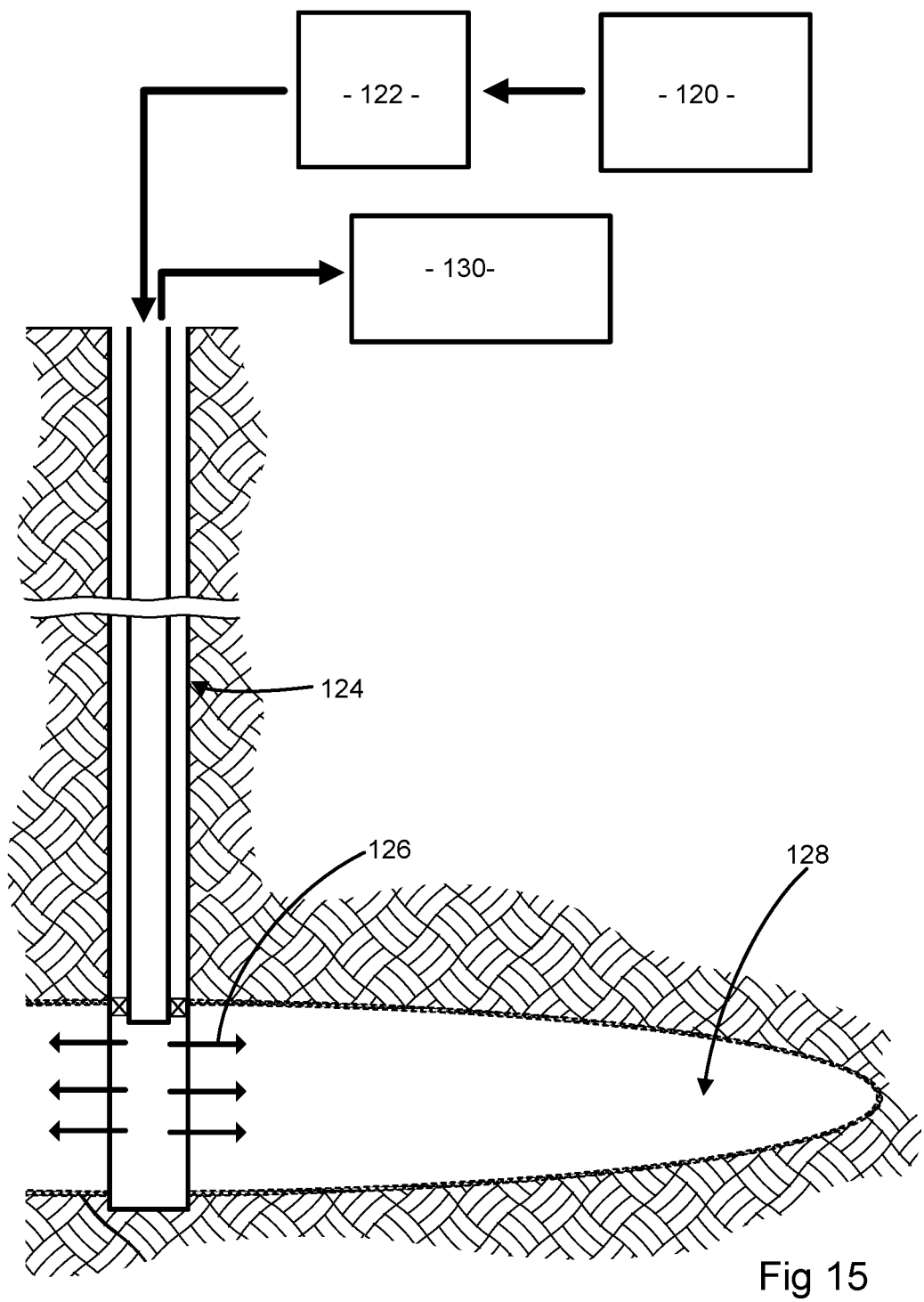
FIG. 15 is a section through the earth schematically showing a hydraulic fracturing operation.

FIG. 15 shows schematically a hydraulic fracturing operation. As is well-known in the industry, viscosifying polymer is mixed with water in mixing plant 120 and is pumped down wellbore 124 under pressure by pumps 122. It flows out as indicated at 126 into the formation downhole thereby creating a fracture 128. Subsequently, pumping stops and the hydrostatic pressure downhole forces flow back to the surface where the returning flow passes through equipment 130 which may measure the volume of flow returning to the surface. Samples of the returning flow are taken here, the aqueous phase in the samples is separated from any oil, and the aqueous liquid is examined for birefringence by means of the apparatus and method described above with reference to FIGS. 2 to 10 so as to determine polymer concentration.

A number of experiments were carried out using the apparatus as shown in FIGS. 2 to 10 to examine samples of aqueous liquid collected at producing wells in an oilfield where an EOR polymer flood operation was in progress. This polymer flood operation was being carried out using FP5115 which was a terpolymer of acrylamide, sodium acrylate and acrylamide-tert-butyl sulfonate which has previously been found to have similar behaviour to partially hydrated polyacrylamide with mean molecular mass of 11 MDa.

Figure 16:
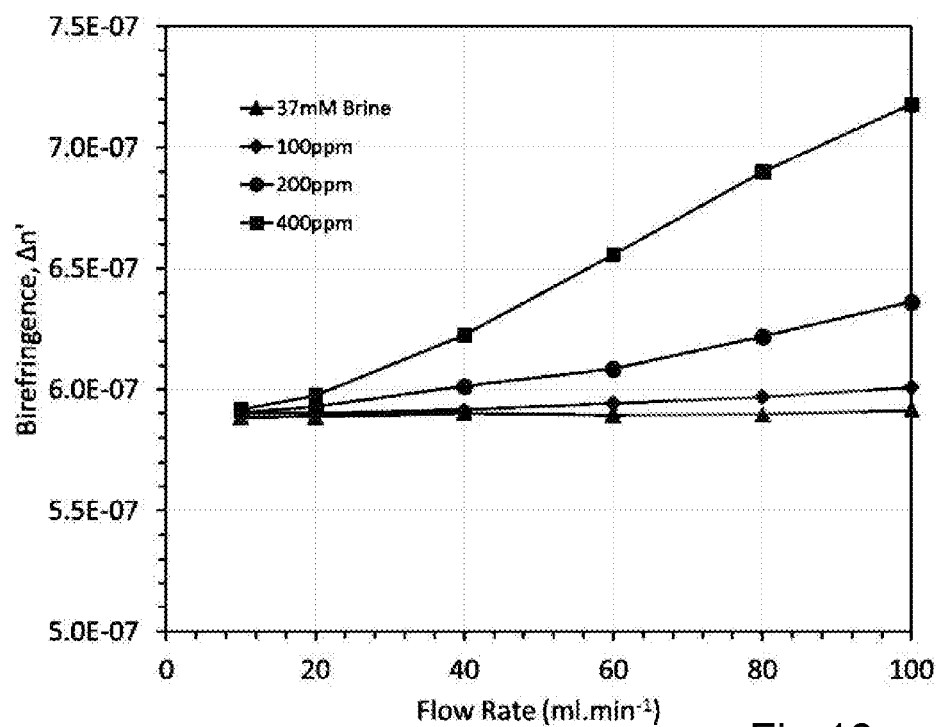
FIG. 16 is a graph of birefringence plotted against flow rates for various concentrations used for calibration

For the purpose of calibration, solutions of this polymer were made in brine chosen to have similar content of calcium and potassium ions and similar ionic strength to brine which was being produced from the reservoir. FIG. 16 is a plot of birefringence values determined using various concentrations of FP5115 polymer in this brine.

Figure 17:
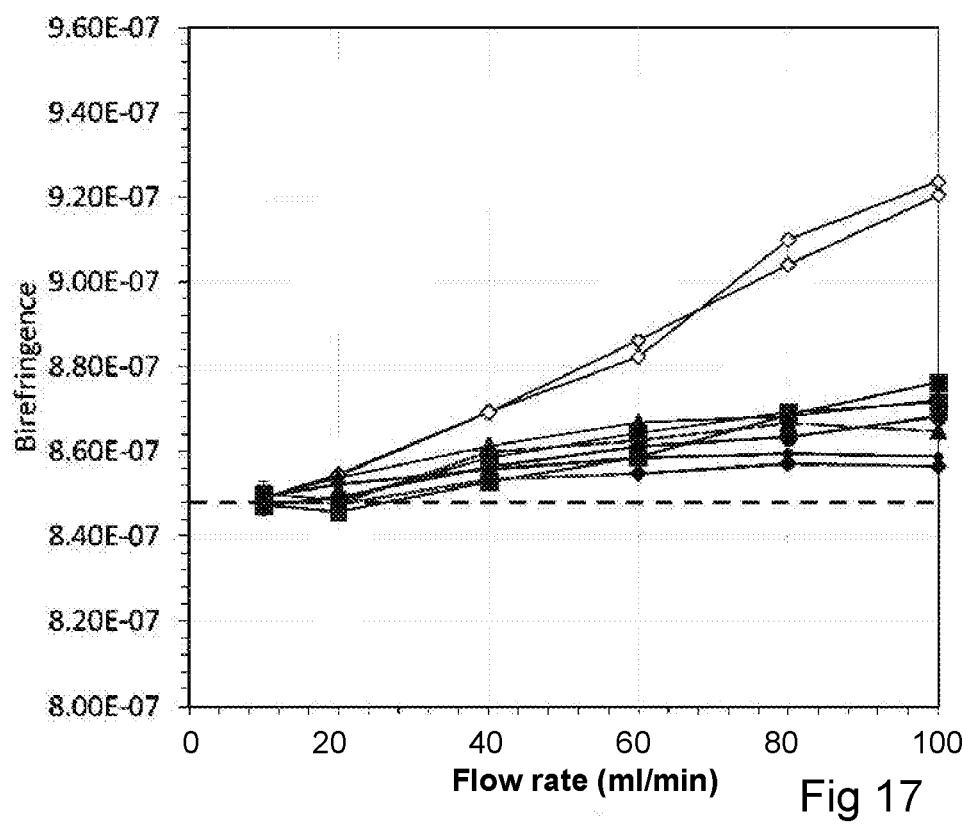
FIG. 17 is a graph of birefringence plotted against flow rates for samples collected from one well on a succession of days.

Samples of aqueous phase were collected daily during an 8 day period from three producing wells referred to here as wells A, B and C. The oilfield had four injection wells arranged at roughly the corners of a square. Well A was inside the square, well B was outside the square and well C was also outside the square and further from it. The samples were collected by a procedure intended to minimize shear of the liquid. On one day a sample was also collected from the supply to one of the injection wells to provide a comparison. After an initial separation of aqueous liquid from oil, a small quantity of a hydrophobic solvent was added to each sample which was then shaken and centrifuged. The hydrophobic solvent and centrifuging assisted the removal of both small droplets of oil and small solid particles from the aqueous liquid. Each sample of aqueous liquid was then examined for fluorescence using the same apparatus and using several flow rates. FIG. 17 shows the results from well A and the sample from an injection well plotted as a graph.

Figure 18:
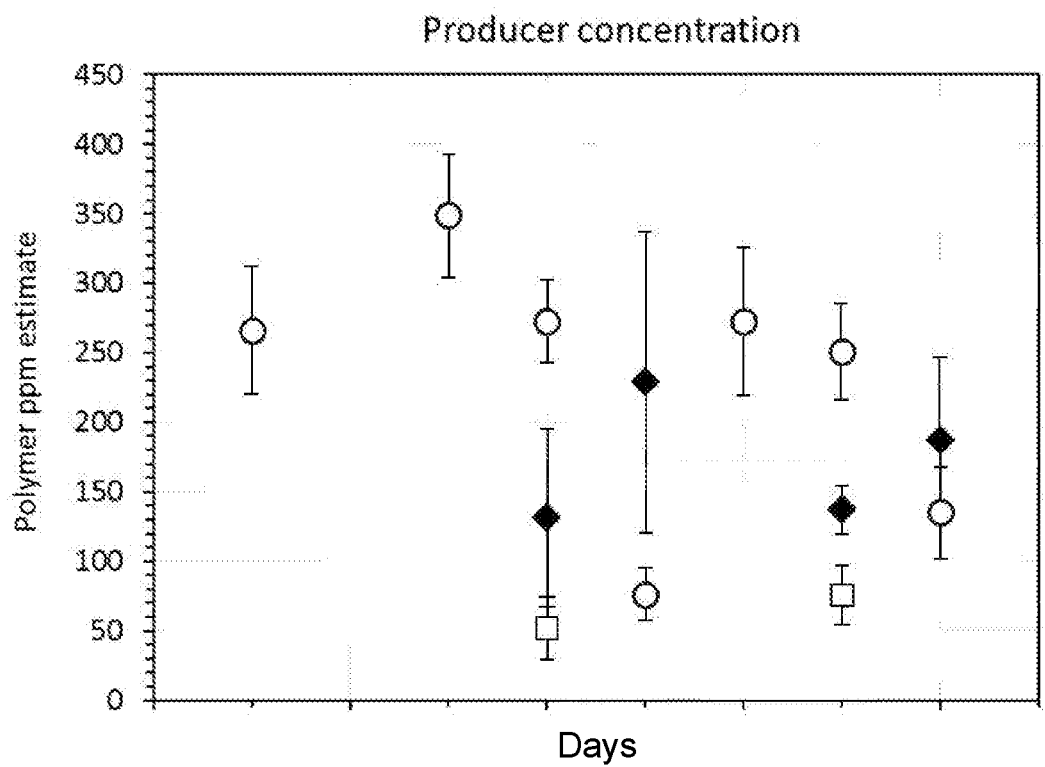
FIG. 18 is a chart of concentrations of polymer calculated from the samples collected from each of three wells on successive days.

Polymer concentrations were calculated from the results for each day for each well. For wells B and C it was not possible to get reliable results on each day. The results, with error bars are shown in FIG. 18. Results for well A are shown as open circles, results for well B are shown as solid diamond and results for well C are shown as open squares. Mean values over the period were calculated. These calculated means were 233 ppm, 68 ppm and 25 ppm for wells A, B and C respectively.

This was a stringent test because at the time these measurements were carried out the injected polymer concentration had been reduced to 312 ppm from the initial design concentration of 1500 ppm. Nevertheless it was possible to detect and measure concentrations of polymer in both well A and well B and it was even possible to detect polymer in Well C where the polymer concentration was very low.

The description above has focused on embodiments using birefringence to measure polymer concentration. There are a number of further possibilities within this disclosure.

Although the properties of a viscosifying polymer used in an oilfield procedure are known before the polymer is put to use, it is possible that the polymer will be degraded during flow or by chemical reaction underground, leading to reduction of its molecular weight. The detection of polymer presence and properties at both surveillance and production wells may be used to update and history-match the reservoir models used to design and optimize subsequent injections or slugs of the EOR fluid.

Pressure drop through the slot 36 can be measured using pressure sensors at the side branches 46. If the pressure drop and the rate of flow through the slot 36 are both known, it is possible to make a determination of solution viscosity. This can be combined with the birefringence measurement to calculate both concentration and molecular mass of the polymer in the solution which is being examined.

Referring back to equation (9) quoted earlier, birefringence $\Delta n$ is given by:

$$\Delta n = \frac{2\pi c N_A}{15 M n}(n_I^2 + 2)^2 (\alpha_1 - \alpha_2) \frac{l^2}{l_{RC}^2} \quad (9)$$

where $n_1$ is the isotropic refractive index of the solution. Two extreme cases illustrate the strong sensitivity of $\Delta n$ to chain conformation, as follows. For weak extensional flow such that chain length l is not much greater than the length of a randomly coiled molecule $l_{RC}$, equation (9) gives:

$$\Delta n_{WEAK} = \frac{2\pi c N_A}{15 M n}(n_I^2 + 2)^2 (\alpha_1 - \alpha_2) \quad (12)$$

whereas for strong extensional flow, when the polymer chain is almost fully extended, l approximates to $l_0 M/m$, and Eq. 9 gives $$\Delta n_{STRONG} = \frac{2\pi c N_A}{15 n}(n_I^2 + 2)^2 (\alpha_1 - \alpha_2). \quad (13)$$

These two equations show $\Delta n_{STRONG}$ to exceed $\Delta n_{WEAK}$ by a factor of M, e.g. by typically a factor of $10^5$ to $2\times 10^7$, hence making $\Delta n_{STRONG}$ very sensitive to the polymer's molecular mass, thus also making the birefringence a sensitive indicator of the degradation of molecular mass.

Anisotropic polarizability of polymer molecules may be observed as a dielectric property such as conductivity or permittivity. If a solution containing polymer molecules aligned with the flow direction by means of extensional flow is exposed to an alternating electrical field at a frequency which is below optical frequency but much higher than the relaxation frequency originating from any permanent dipole moment possessed by the polymer chain, there will be a dielectric response from the atomic polarizability. This response will be anisotropic and can be observed as a dielectric property along the direction of the polymer chains' length which is greater than the same dielectric property transverse to the chains length. Indeed the dielectric property transverse to the chains length may have a negligible or zero value because orientation of molecules or parts of molecules transverse to chain length is random.

Figure 19:
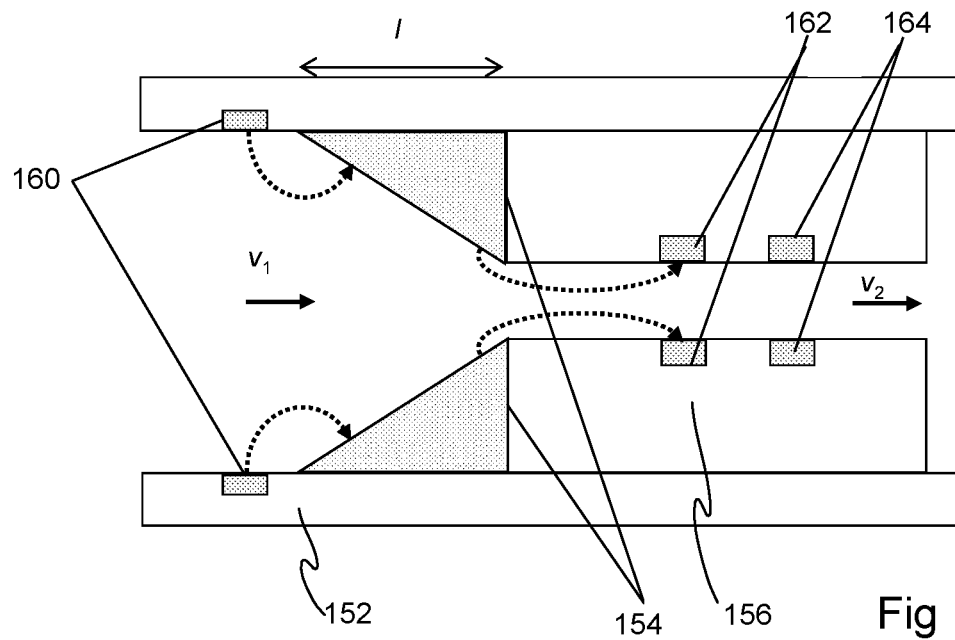
FIG. 19 is a sectional view of a flow cell equipped with electrodes for permittivity measurement.

FIG. 19 shows a flow cell which may be used to measure anisotropy of permittivity which is a dielectric property. This cell differs from those shown in FIGS. 1 to 8 in that it is cylindrically symmetric around the flow direction. The entry flow is along the axis of a cylindrical pipe 152 of diameter $d_1$. This contains a circularly symmetrical constriction 154 leading to an exit duct 156 of diameter $d_2$. The constriction causes extensional flow in which there is extension in the flow direction and contractional flow in all directions orthogonal to the flow direction. The axial extensional flow rate is given approximately by $$\dot{\varepsilon}_z = \frac{v_2 - v_1}{l} = \frac{v_1}{l}[(d_1/d_2)^2 - 1] \quad (14)$$

where $v_1$ is the entry fluid velocity, $v_2$ is the exit fluid velocity, and l is the axial distance over which the diameter tapers from $d_1$ to $d_2$.

The cylindrical pipe 152 and the exit duct 156 are made of electrically insulating material. The cell has four electrically conductive annular electrodes. The electrode 160 is in the upstream region where extensional flow has not begun and the centre-line velocity is $v_1$. The tapering constriction 154 is formed of electrically conductive material and is used as an electrode. The next two annular electrodes 162 and 164 are set in the exit duct 156 where the centre-line velocity is $v_2$. Thus dielectric measurements (relative to $v_1=0$) made between the electrodes 160 and 154 reveal the stretching of the polymer molecules by the axial extensional flow, while measurements (relative to $v_1=0$) made between the electrodes 154 and 162 and measurements between the electrodes 162 and 164 reveal how the stretched molecules revert to their unstretched or randomly-coiled state in the time after being stretched. Both measurements depend on the molecular mass of the polymer, and so relate to its ability to viscosify a solvent. In FIG. 19 the dotted lines show the approximate paths of current flow between the electrodes.

For sub-optical frequencies, but for those much higher than the relaxation frequency originating from any permanent dipole possessed by the polymer chain, we may expect a dielectric response from the atomic polarizability that resembles those described by Eqs 12 and 13, but where the term $\alpha 1 - \alpha_2$ is replaced by the anisotropy $\beta_1 - \beta_2$ of the atomic polarizability of a repeat unit. Thus, the essential dependence on molecular mass shown by Eqs 12 and 13 will be preserved at lower frequencies. Consequently, the extensional flow induced anisotropy of permittivity arising from the atomic polarizability anisotropy will also be a sensitive indicator of the degradation of molecular mass.

Figure 20:
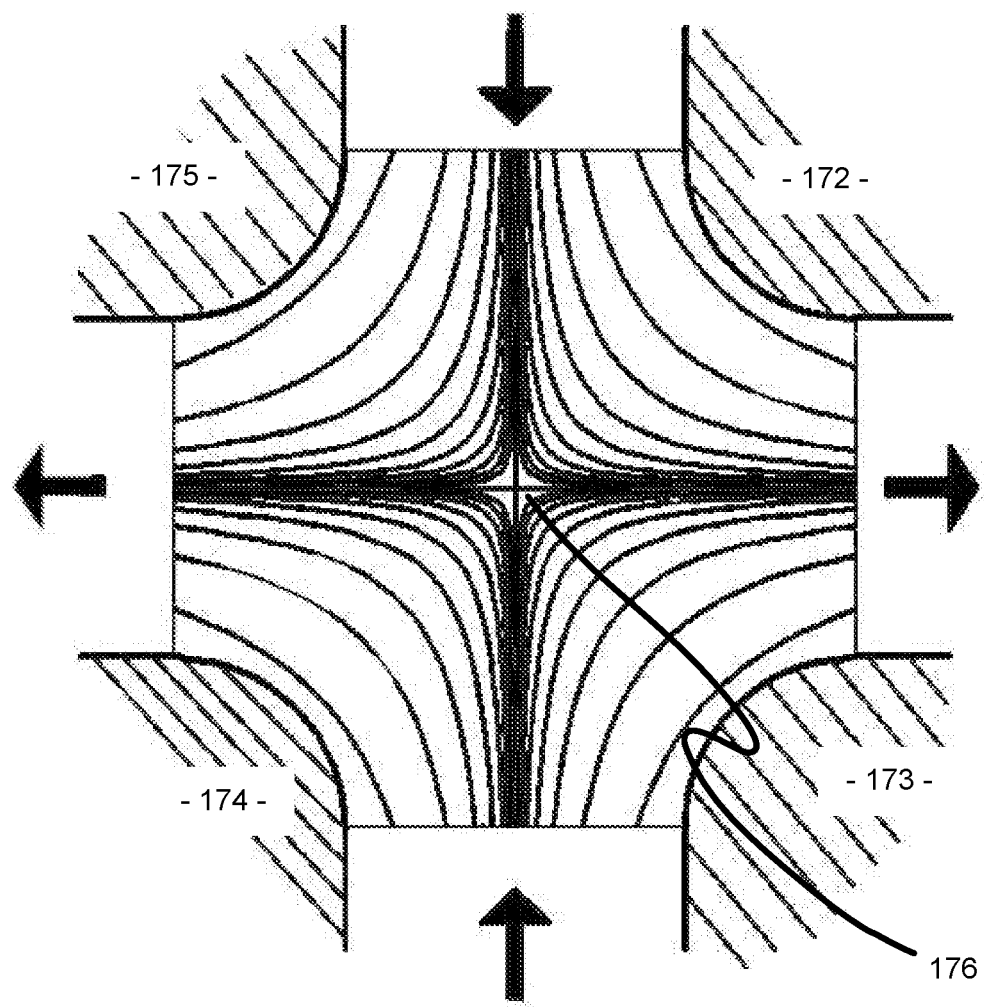
FIG. 20 diagrammatically shows a crossed slot arrangement for generating extensional flow.

In embodiments of the present disclosure, the EOR sensor may comprise an optical birefringence sensor utilising biaxial extensional flow. In such embodiments, the crossed slots method may be preferred on account of its absence of moving parts and its robustness. A crossed slots extensional flow birefringence sensor is illustrated in FIG. 20, where the flow-lines are in a crossed-slots geometry. This figure is a section of a three-dimensional apparatus in which the rigid elements 172, 173, 174, and 17 which define the slots run normally into the plane of the figure.

For an average liquid velocity vAV in the inlet or outlet slit of width w, the central extensional flow rate is given by:

$$\dot{\varepsilon} = \frac{2 v_{AV}}{w}. \quad (15)$$

In the optical embodiment utilizing biaxial extensional flow, a narrow beam of polarized light passes through the apparatus, normal to the plane of the figure, and centered on the region denoted by 176. The principal refractive indices $n_1$ and $n_2$ are parallel to the principal flow directions indicated by the bold arrows, i.e. parallel to the principal stretching and contraction directions of the polymer. The birefringence $\Delta n = n_1 - n_2$ may be measured by conventional methods. For example, birefringence may be measured by measuring the changes in the polarization of light passing through the material being tested. Birefringence can also be measured using dual polarization interferometry.

In the dielectric embodiment utilizing biaxial extensional flow the rigid elements 172, 173, 174, and 175 are made of a conductive solid material insulated from each other by other rigid elements (not shown). Thus various dielectric aspects of the effect of the extensional flow in their stretched or unstretched (randomly-coiled) state of the molecules may be detected. Such measurements (as discussed above) depend on the molecular mass of the polymer, and so relate to its ability to viscosify its solvent.

The example embodiments described in detail above can be modified and varied within the scope of the concepts which they exemplify. Features referred to above or shown in individual embodiments above may be used separately or together in any combination so far as this is possible. Accordingly, all such modifications are intended to be included within the scope of this disclosure as defined in the following claims.

The invention claimed is:

1. A method of examining aqueous liquid, the method comprising:
    collecting a sample solution of an aqueous liquid after contact between the aqueous liquid and a subterranean geological formation;
    flowing the sample solution of the aqueous liquid through a constriction thereby causing extensional flow and alignment of any polymer molecules with the flow;
    examining the sample solution for at least one anisotropic physical property of the any aligned polymer molecules in the collected sample solution when flowing through the constriction; and
    measuring polymer within the sample solution by using the at least one anisotropic physical property to determine at least one of concentration of polymer in the solution or molecular mass of the polymer in the solution.

2. The method of claim 1, wherein the subterranean geological formation is a hydrocarbon reservoir and collecting the sample solution is performed within the hydrocarbon reservoir or from liquid produced to surface from the hydrocarbon reservoir.

3. The method of claim 1, wherein examining the sample solution for the at least one anisotropic physical property of the any aligned polymer molecules comprises examining the sample solution for birefringence of the any aligned polymer molecules.

4. The method of claim 3, wherein examining the sample solution for at least one anisotropic physical property of the any aligned polymer molecules comprises:
    directing a beam of light from a light source through at least one first optical component to generate a defined polarization state, then through the sample solution in the vicinity of the constriction such that any polymer molecules in the sample solution are aligned with the flow, then through at least one second optical component that enables determination of a resultant polarization state; and
    determining the birefringence from the resultant polarization state.

5. The method of claim 4, wherein the at least one first optical component comprises a linear polarizing filter.

6. The method of claim 4, wherein the at least one second optical component comprises a linear polarizing filter.

7. The method of claim 4, further comprising:
    measuring an intensity of light from the light source and an intensity of light passing the at least one second optical component; and
    determining an amount of the birefringence from a ratio of the measured intensities.

8. The method of claim 4, wherein the light source is a laser.

9. The method of claim 4, wherein the second optical component is optically configured to pass no light therethrough when no polymer is present.

10. The method of claim 1, wherein a concentration of the polymer in the aqueous liquid is less than 1% by weight.

11. The method of claim 1, wherein the polymer is formed of repeat units which each have a molecular mass not exceeding 300 Da and the polymer has a mean molecular mass of at least 3.5 MDa.

12. The method of claim 1, further comprising:
    pretreating the sample solution of the aqueous liquid before flowing it through the constriction, the pretreating comprising removing solid particles and hydrophobic liquid droplets from the sample solution.

13. The method of claim 12, wherein the sample solution of the aqueous liquid continues to contain dissolved salts from the subterranean geological formation when the sample solution flows through the constriction after pretreatment.

14. The method of claim 1, wherein examining the sample solution for the at least one anisotropic physical property includes measuring a dielectric property by:
    measuring polymer stretching by performing dielectric measurements on the sample solution before and at the constriction;
    measuring reversion of the polymer to unstretched or randomly-coiled state by performing dielectric measurements on the sample solution after the constriction.

15. A method of monitoring an operation to recover hydrocarbon from a subterranean reservoir, the method comprising:
    injecting an aqueous solution of viscosifying polymer into the reservoir through at least one wellbore so that the aqueous solution of viscosifying polymer travels through the reservoir toward at least one other wellbore; and
    collecting aqueous liquid from the at least one other wellbore and examining the aqueous liquid for the viscosifying polymer by the method of claim 1.

16. The method of claim 15, wherein the aqueous solution of viscosifying polymer injected into the reservoir comprises not more than 3% by weight of viscosifying polymer.

17. The method of claim 15, wherein the aqueous solution of viscosifying polymer injected into the reservoir comprises not more than 1% by weight of viscosifying polymer formed of repeat units which each have a molecular mass not exceeding 300 Da and the polymer has a molecular mass of at least 3.5 MDa.

18. The method of claim 15, further comprising:
    measuring polymer degradation by detecting polymer presence and concentration at both surveillance and production wells of the at least one other wellbore.

19. A method of examining flow back of liquid from a hydraulic fracturing operation which comprises pumping aqueous liquid viscosified with polymer into a reservoir, the method comprising:
    collecting samples of aqueous liquid from the flow back; and
    measuring the concentration of viscosifying polymer in the samples by the method of claim 1.

20. The method of claim 1, further comprising measuring pressure drop across the constriction and using the pressure drop and rate of flow through the constriction to determine solution viscosity.

* * * * *